United States Patent [19]

Lemelson

[11] Patent Number: 4,803,992
[45] Date of Patent: Feb. 14, 1989

[54] ELECTRO-OPTICAL INSTRUMENTS AND METHODS FOR PRODUCING SAME

[76] Inventor: Jerome H. Lemelson, 48 Parkside Dr., Princeton, N.J. 08540

[21] Appl. No.: 857,055

[22] Filed: Apr. 29, 1986

Related U.S. Application Data

[63] Continuation-in-part of Ser. No. 848,024, Apr. 3, 1986, and a continuation-in-part of Ser. No. 843,990, Mar. 25, 1986, which is a continuation-in-part of Ser. No. 636,239, Jul. 31, 1984, Pat. No. 4,578,061, which is a continuation of Ser. No. 201,531, Oct. 28, 1980, Pat. No. 4,588,395.

[51] Int. Cl.⁴ .............................................. A61B 5/02
[52] U.S. Cl. ................................. 128/634; 128/666; 128/667; 128/675; 128/748
[58] Field of Search ............... 128/633, 634, 666, 667, 128/675, 748

[56] References Cited

U.S. PATENT DOCUMENTS

| 3,068,739 | 12/1962 | Hicks et al. | 128/634 |
| 3,068,742 | 12/1962 | Hicks et al. | 128/634 |
| 3,123,066 | 3/1964 | Brumley | 128/634 |
| 3,273,447 | 9/1966 | Frank | 128/675 |
| 3,814,081 | 6/1974 | Mori | 128/634 |
| 4,201,222 | 5/1980 | Haase | 128/667 |
| 4,210,029 | 7/1980 | Porter | 128/634 |
| 4,611,600 | 9/1986 | Cohen | 128/667 |

OTHER PUBLICATIONS

Matsumoto et al., J. Med. Eng. and Technol. (GB), vol. 2, No. 5, Sep. 1978, pp. 239–242.

Primary Examiner—Francis J. Jaworski
Assistant Examiner—John C. Hanley

[57] ABSTRACT

Improvements in catheters, particularly of the electro-optical type employing light energy and detect and measure body variables, such as blood pressure and flow and the composition of body fluid. Catheter head and medical instrument structures are provided which may be easily fabricated at low cost to receive and hold light pipes and to contain or define optical components, such as reflectors, lenses and the like, to permit their use in detecting such variables while the instrument or catheter is located in the body. Improvements are also provided in the structures of instrument capsules adapted to be swallowed and allowed to pass through the digestive tract for the purpose of detecting body variables such as the composition of body fluid and tissue.

8 Claims, 3 Drawing Sheets

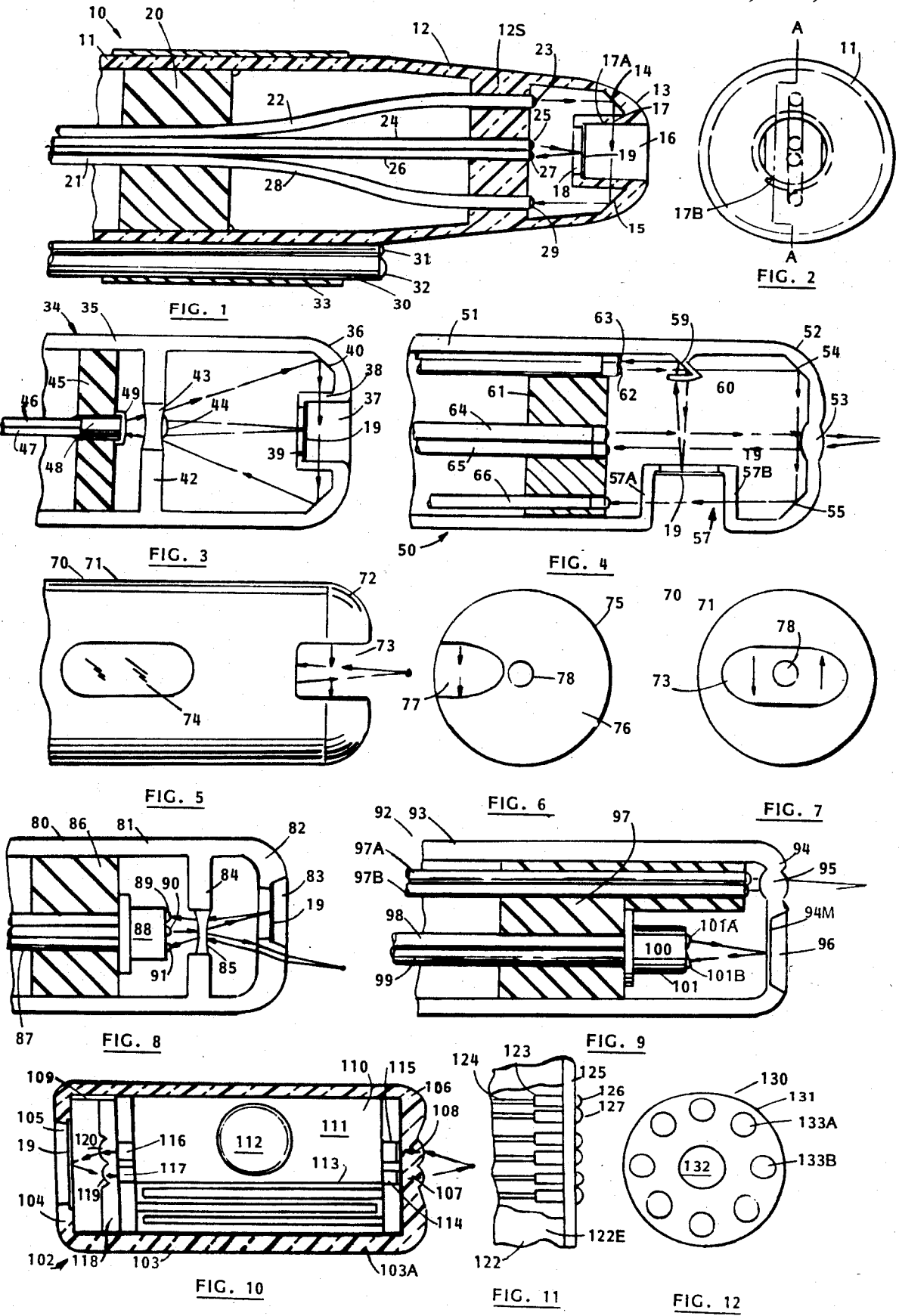

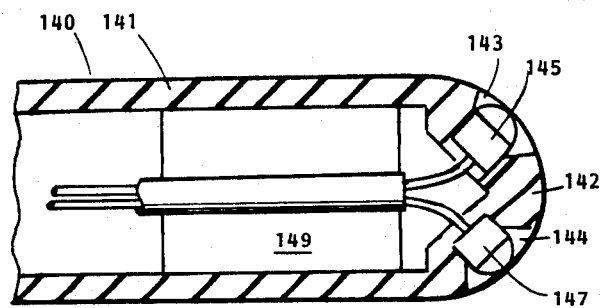
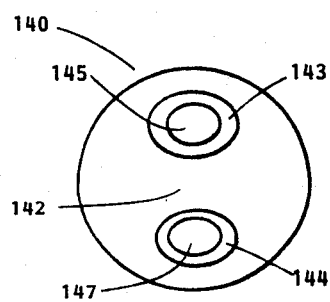
FIG. 13
FIG. 14
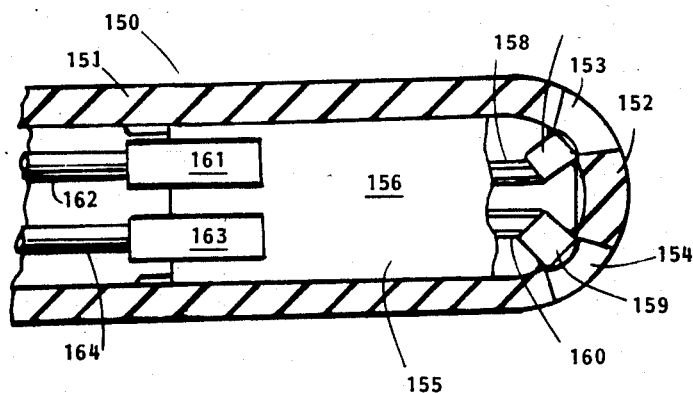
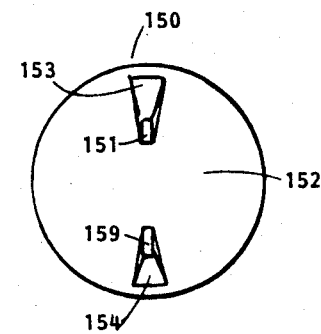
FIG. 15
FIG. 16

ELECTRO-OPTICAL INSTRUMENTS AND METHODS FOR PRODUCING SAME

BACKGROUND OF THE INVENTION

1. Field of the Invention

This invention is in the field of medical instruments including catheters, which are particularly useful in sensing variables existing in living beings, such as the composition of blood and body fluid, contents of the digestive tract and the like, fluid pressure in a body duct and the condition of tissue, such as the lining of the digestive tract and the condition of blood vessels and their contents by visual and computer analysis.

2. The Prior Art

The prior art consists of catheters and instruments provided with light transmission and receiving means for viaually inspecting body ducts. Such devices as boroscopes and endoscopes as well as other medical instruments, have employed means, insertable into a body duct through a natural opening or incision made by a tool, for illuminating a portion of the interior of the duct and receiving light energy for providing a visual indication of the material in the duct and the duct wall to a person using such instrument.

SUMMARY OF THE INVENTION

This invention relates to new and improved structures in medical instruments and methods for fabricating same whereby they are improved in their operation and simplified in their structure and assemblyin a manner suchas to reduce their cost to manufacture.

It is known in the art to produce medical instruments, such as catheters and a variety of other instruments which employ light for the purpose of performing viewing and detecting operations with respect to body fluid and tissue associated with a living being for the purpose of detecting specific elements or compositions and diagnosing various conditions and maladies. Light pipes, such as flexible bundles of optical fibers, have been used in endoscopes and the like to permit a physician to view matter within a body such, such as select portions of the digestive tract including the wall thereof, on a viewing screen located at the end of the instruments which is exterior of the body during its use. Light pipe containing catheters have also be employed to view the interiors of body ducts and to direct laser generated light energy to select locations of body ducts for performing such operations as destroying blood clots, corterizing wounds and the like.

The instant invention is concerned with improving the constructions of medical instruments which are particularly used to transmit and receive light, to render them easier to assemble, calibrate, use and maintain than similar instruments of the prior art and to fabricate at lower cost. The improved medical instruments, including catheters, may be employed to perform either or both of two primary functions, to inspect a body duct and/or its contents and to provide and direct intense radiation, such as laser generated light, against select matter existing within bodyducts for the purpose of operating on same, such as by heating, vaporinzing or buring same, such as in the performance of a tissue repair or removal operation thereon, a corterizing operation, a blood clot removing operation, or an inspection operation involving the vaproization or burning of tissue or body fluid.

Accordingly it is a primary object of this invention to provide new and improved structures and constructions in medical instruements including catheters and other instruments which are intended to be partly inserted into a body cavity or duct and utilize optical and/or electro-optical means for inspecting or viewing and/or otherwise operating on body matter with light.

Another object is to provide improvements in catheters employing photooptical means for detecting body tissue and body fluid variables.

Another object is to provide electro-optical instruments of simplified construction.

Another object is to provide medical catheters and the like which may detect a plurality of variables employing light energy which is varied or modulated to effect such detection.

Another object is to provide photo-optical devices which are simple in structure and relatively low in cost.

Another object is to provide low cost expendable catheters for use in detecting biological elements in body fluids.

Another object is to provide improved constructions in medical instruments which utilize light to detect body variables wherein housing for such instruments are of molded construction and contain select molded portions which receive and guide light for detection purposes.

Another object is to provide a medical instrument capable of simultaneously detecting body fluid pressure and one or more variables defining the composition of body fluid.

Another object is to proide improved constructions in electro-optical instruments employing one or more light pipes, such as fiber optic bundles, wherein such light pipes are supported and aligned within a molded housing by portions of the housing.

Another object is to provide a medical instrument which is capable of detecting both body temperature and fluid pressure or heart rate simultaneously.

Another object is to provide improvements in the construction of medical capsules.

Another object is to provide improved methods for detecting fluid pressure and flow simultaneously using a single instrument.

With the above and such other objects in view as may hereinafter more fully appear from studying the specification and drawings, the invention consists of the novel constructions and combinations of parts as will be more fully described hereafter, but it is to be understood that changes and modifications may be resorted to which come within the scope of the claims.

BRIEF DESCRIPTIONS OF THE DRAWINGS

FIG. 1 is a side view with parts broken away and sectioned of part of the operating end of a medical catheter operable to photo-optically detect both body fluid pressure and composition.

FIG. 2 is an end view of the catheter of FIG. 1.

FIG. 3 is a side view of a portion of a medical instrument, such as the operating head of a catheter which is a modified form of that shown in FIG. 1.

FIG. 4 is a side view in cross section of a modified form of the catheters of FIGS. 1 and 3.

FIG. 5 is a partial side view of the operating end of a catheter which is a modified form of that shown in FIG. 4.

FIG. 6 is an end view of a catheter which is a modified form of the catheter shown in FIG. 5.

FIG. 7 is an end view of a catheter which is a modified form of that shown in FIGS. 5 and 6.

FIG. 8 is a partial side view of the operating end of a catheter which is a modified form of the catheter shown in FIG. 3.

FIG. 9 is a side view of a catheter which is a modified form of that shown in FIG. 8.

FIG. 10 is a side view in cross section of an instrument in the form of a capsules adapted to be injested and to travel through the digestive tract and operable to sense a plurality of body variables.

FIG. 11 is a partial side view of an array of photo-optical scanning devices mounted on a substrate such as a portion of one of the housings shown in FIGS. 1 and 10.

FIG. 12 is a front view of a circular array of photoelectric detectors applicable to the embodiments of FIGS. 9 and 10.

FIG. 13 is a partial side view in cross section of the operating end of a medical instrument operable to detect both body temperature and body fluid pressure such as blood pulse.

FIG. 14 is an end view of the device of FIG. 13.

FIG. 15 is a partial side view in cross section of a modified form of embodiment of FIGS. 13 and 14 and FIG. 16 is a front view of the device of FIG. 15.

Figure 17:
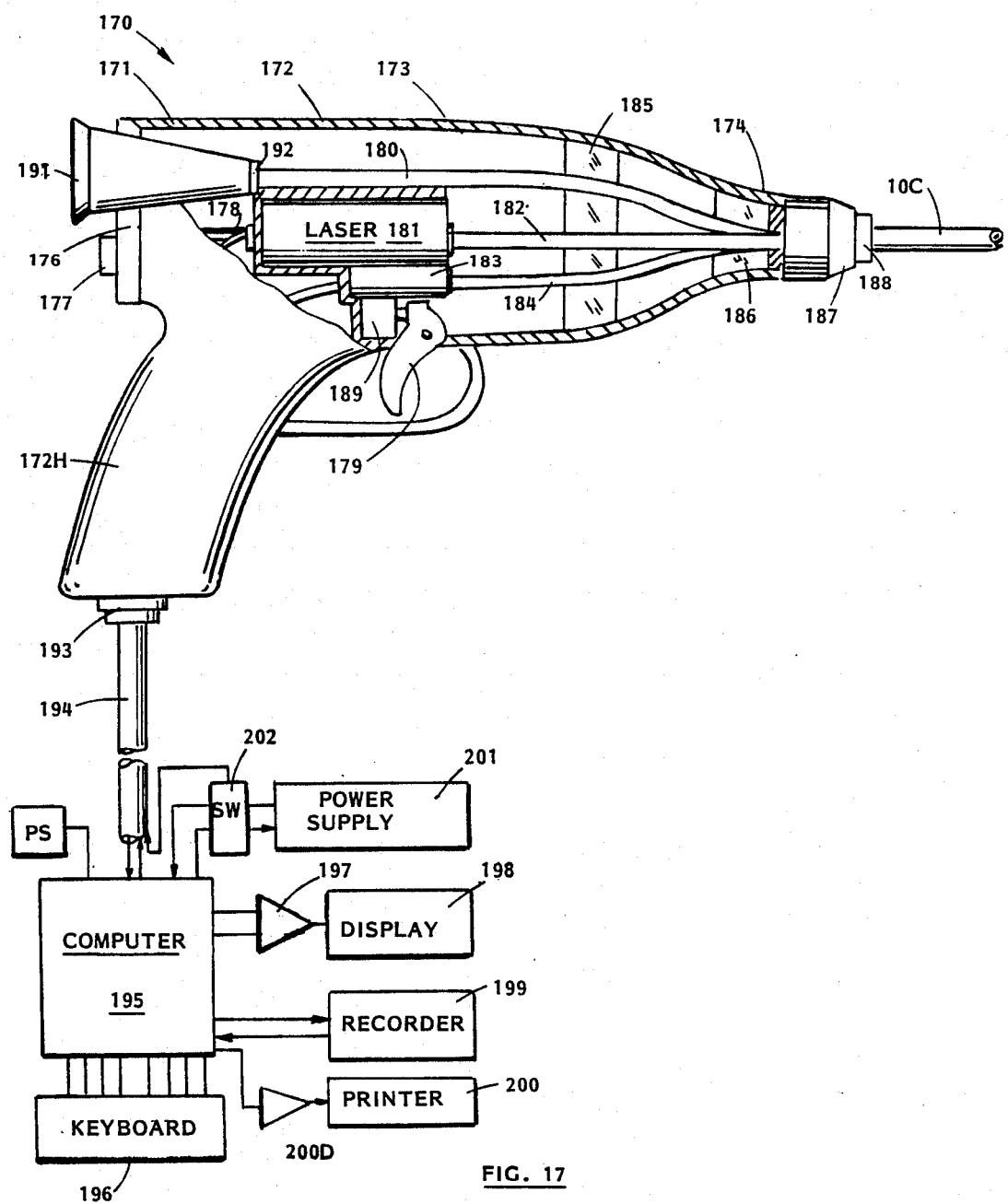
FIG. 17 is a side view of a hand-holdable piston-like housing with parts broken away for clarity showing instrumentation including a computer, display and recording means connected thereto for use with the catheters of FIGS. 1–9 and 13–16.

In FIG. 1 is shown the operating end of an instrument or device 10, such as a catheter or other form of instrument which is adapted to be inserted into a body cavity, a wound or incision formed by surgery in a living being. The device 10 may also be utilized, as described hereafter, to measure a plurality of variables with respect to non-living material.

Device 10 includes an elongated housing 11, illustrated as having a cylindrical wall with a tapered forward end 12, the end 13 of which is smoothly rounded to permit it to pass through, for example, a body cavity of similar or greater diameter than the diameter or cross section of the device.

If the device 10 is a catheter, a cable 21 extending from the rear end [not shown] of the flexible catheter tube assembly, terminates near the end 13 of the operating hed, as shown, and is formed of four separate flexible light pipes denoted 22, 24, 26 and 28. The ends of such flexible light pipes are formed with respective lenses denoted 23, 25, 27 and 29 and are held in fixed longitudinal attitudes in respective receptacles formed of passageways extending through an interior bulkhead or wall 12S which is illustrated as being molded of the same material forming the side wall of the operating head, it being noted that such material is preferably a rigid or semi-rigid transparent, light transmitting plastic and the operating head is molded of two half-sections, of substantially semi-cylindrical shape, which are aligned and joined together to form the cylindrical housing, preferably by adhesive bonding, ultrasonic or radio frequency welding.

Formed in the front end portion 13 of the housing 11 is an indentation or cavity 16 having a somewhat cylindrically shaped circumscribing side wall 17 containing laterally opposed and aligned flat wall portions 17A and 17B which define windows through which light energy may pass to be directed through and across the cavity 16 for scanning fluent material, such as body fluid, existing in such cavity. The bottom wall 18 of the indentation defining the cavity 16 is formed with a central recess 18A or opening therein across which opening is disposed a thin, disc-shaped plate or membrane 19 which may deflect with variations in fluid pressure applied thereto through the fluid in the cavity 16. Such variations in fluid pressure may be detected photo-optically exterior of the operating head or catheter 11 by means of light, such as laser light, directed through the light pipe or fiber optic bundle 24 from a laser disposed at the other end of such light pipe, such as exteriorallyof the instrument or catheter. Such light is directed by means of lens 25 against the inside surface of the thin plate or membrane 19 and is reflected therefrom to the receiving lens 27 of the light pipe 26 whereafter it passes along the light pipe to the other end thereof at which other end is located a photoelectric detector, such as a photo-diode [not shown] which converts variations in such reflected light to variable electrical signals which are computer processed and analyzed to provide digital electrical signals indicative of the degree of deflection of the diaphragm 19, which are an indication of the fluid pressure applied thereto.

The apparatus 10 also contains a plurality of reflecting surfaces 14 and 15, formed by properly molding the front end of the inside surface of the housing, for respectively receiving light energy passed through the lens 23 of the light pipe 22 from a source of light, such as a laser or other source, located at the other end of light pipe 22, which light is directed as a beam against the reflecting surface 14 as reflected through the flat window portion 17A of the side wall, then passes through the interior of the cavity 16 to the flat window portion 17B formed in the opposite portion of the side wall 17 where it passes into the interior volume at the end of the operating head and is reflected off reflecting surface 15 formed of the inside surface of the end wall 13, then, such light is directed to the receiving lens 29 of the light pipe 28 along which it passes to a photoelectric detector [not shown] which is coupled to the other end of light pipe 28. In other words, light directed along and from the end of light pipe 22 is reflected through fluid, such as body liquid existing in cavity 16 and is nodulated by the physical and chemical contents of such body fluid, causing variations in the content of such light, which variations may be detected by one or more techniques including computerized signal analysis of the electrical signals generated when themodulated light is converted to electrical signals. Furthermore, such received light may also be spectrographically analyzed to permit the light passing through the fluid sample to detect both physical and chemical variables present in the fluid being scanned thereby.

By utilizing the detection means and arrangement of components illustrated in FIGS. 1 and 2, fluid pressure and one or a number of physical and chemical variables present in such fluid, may be simultaneously detected within a duct, such as a blood vessel, intestinal tract or other body duct, without resort to a plurality of devices and assemblies.

Also illustrated in the embodiment of FIGS. 1 and 2, is a flexible cable 30 secured to and extending along the outside surface of the instrument or catheter 11 by means of a band 33, such as a strap or plastic film shrunk around the two assemblies, holding the cable tightly against the outside surface of the housing defining the instrument. Cable 30 contains a light source 31 and a viewing optical assembly 32 of a multitude of light pipes, for receiving light from such light source after it has reflected off surfaces in the vicinity of the end of the assembly 11 to permit a person at the other end of the instrument or light pipe to view the wall of the body duct so as to properly locate the catheter and position the operating head thereof at a select location within the body duct. Accordingly, coupled to the opposite end of the cable 30 is a light source for directing light along the flexible light pipe 31 and an eyepiece with suitable optics for providing an image on a viewing screen thereof, of light directed through themultiple optical fibers of the light pipe 32.

In FIG. 3 is shown a modified form of the instrument illustrated in FIGS. 1 and 2 which comprises a catheter 34 or otherform of instrument, having a cylindrical wall 35 defining the operating end of such catheter or instrument and formed of a transparent rigid or semi-rigid self-supporting plastic. The end wall 36 of the operating head of the instrument is rounded and contains a centrally formed cavity 37 in the circumscribing side wall 38 formed in the manner of the side wall 17 of the cavity 16 of FIG. 1 and operable to permit a beam of light to pass laterally across such cavity, as illustrated. A plurality of light pipes or fiber optic bundles, denoted 46 and 47, respectively conduct light, such as laser light, froma source of such light to the end 48 of the assembly of light pipes and receive such light after it has passed throug hfluid or liquid in the cavity 37 for conducting same back along the light pipe 47 to a photoelectric detector.

Notation 42 refers to a support for a lens formation 43 which, together with such support, are integrally molded of the same light-transmitting plastic forming the side wall 35. The lends formation 43 is operable to receive light from the light pipe 46, direct same along the path illustrated to a reflecting surface 40 formed in the upper portion of the end wall 36, which reflects such light through the flat portion of the side wall 38 surrounding the cavity 37 and across such cavity through the opposite flat formation of the side wall, thence against a reflecting surface 41 forming the inside surface of the end wall 36 and therefrom to the lens formation 43 which directs such reflected light to certain of the fibers of the optical fiber bundle 47 which fibers extend to a receiving photoelectric detector or array of such detectors for either image signal analyzing and/or spectrographic signal analyzing such light to determine certain physical and chemical characteristics. of the matter scanned.

A portion of the light directed from the end of fiber optic bundle 46 is directed through a convex or focusing portion 44 of the lens formation 43 which directs such light against the inside surface of a thinwall or diaphragm forming part of or sealingly attached to the bottom wall 39 of the cavity 37 and communicating with the interior volume of the head of the instrument through an opening therein which opening is positioned to permit such plate or diaphragm to variably deflect with variations in pressure of the body fluid in the cavity 37. Thus light focused by lens formation 44 against the inside surface of the diaphragm 19, is reflected back to such lens formation 44 which refocuses such light through the lens 43 to a second group of receiving optical fibers forming the riber optic bundle 47 and such latter fibers direct such reflected light to a respective photoelectric detector at the other end thereof for detecting same and generating electrical signals which are analyzed to determine the pressure of fluid and/or other variations which occur therein with time. Reflecting surfaces 40 and 41 which respectively direct light to the cavity 37 and from the cavity back to the lens formation 43, are each formed of respective opposed portions of the end wall 36 by molding thus eliminating the need for assembling small mirrors inside the housing.

FIG. 4 illustrates a modified form of the embodiment illustrated in FIGS. 1-3 and comprises an instrument 50 for electro-optically detecting characteristics of matter, such as body fluid existing outside of the instrument, and fluid pressure. The instrument 50 includes an elongated housing 51 having a closed end wall 52 made of light transmitting resin or glass material and having a portion 53 thereof shaped in the form of a focusing lens and a plurality of portions of the end wall interiorally shaped to define respective flat surfaces 54 and 55 which serve to reflect light from one to the other and then along a select path parallel to the central axis of the housing.

Supported by a plurality of spacers, one denoted 61 of which is illustrated and is either formed of or secured to the inside surface of the housing, are five light pipes, preferably formed of bundles of optical fibers and extending parallel to the central axis of the housing from the opposite end thereof [not shown]. A first light pipe 62 is optically coupled to a source of light, such as a laser, and directs light therefrom against a reflecting-transmitting mirror-like formation 59 which may be formed integral with the wall of the housing by molding or may be secured thereto and is operable to pass a portion of the light beam emitted from the light pipe 62 to the mirror surface 54 and a second portion of said light beam to a focusing lens portion 60 which directs such light against the inside surface of a diaphragm 19 which is supported by opposite flat wall portions 57A and 57B which define a lateral channel or recess 57 in the lower portion of the housing 51. The diaphragm, which is mounted in wall 57C joingin the wall portions 57A and 57B, deflects as described, with variations in fluid pressure and such deflections are detected when light which is reflected therefrom passes back through the lens 60 and is reflected off the upper portion of the reflecting surface of the mirror 59 back to the input of the light pipe 63 which directs such light to the other end thereof at which end a photoelectric detector detects and converts the variable light energy to a variable electrical signal which is analyzed as to the volume surrounding the end of the housing 51.

A portion of the light emitted from the end of the light pipe 63 passes completely through the mirror 59 and, as described,is reflected from surfaces 54, 55 and directed laterally through the recess 57 to the input end of the light pipe 66, which pipe extends to a second photoelectric detector located at the other end thereof, which generates a variable electrical signal which varies in accordance with variations in the optical characteristics of the fluid in the recess 57, such as caused by particles and biological elements therein.

Light, such as generated by a laser, is also directed along light pipe 64, through lens 53, a formation molded in the end wall 52 which focuses light against matter exterior of thehousing, such as blood or other fluid containing chemical and biological elements which modulate such focused light and reflect same back to the lens formation 53 which directs such reflected light to the input end of light pipe 65 which extends to a photoelectric detector and/or a spectrographic detector connected to means for analyzing the spectroscopic characteristics of the fluid as defined by the characteristics of the reflected light passed along light pipe 65.

It is briefly noted that a variety of light directing devices, such as lens formations, collecting and transmitting mirror formations, prisms and prismatic formations, diffusers, and light pipes, may be integrally precision molded of light transmitting resinous material forming part of a housing or an insert in a housing, such as one of the types illustrated herein, to properly direct light from one or more sources or light pipes within such housing for performing one or a plurality of different measurement functions of the types described, such as detecting variations in fluid pressure, the physical and chemical contents of fluid disposed exterior of and/or within such housing. Certain of such optical components may also be provided as inserts whch are precision aligned within the optical component or housing by means of extensions of the inside surface of the wall or walls of the housing and/or indentations or channels molded therein to effect the fabrication of the instrument or its components in an efficient, low-cost manner. By way of example, one or more light pipes may be fabricated by extrusion or by molding same integral with the inside surface or surfaces of a tubular housing or housing linner of an instrument or operating head of a catheter and may be utilized for the purposes described to direct light along one or more select paths into such housings and to receive and direct reflected light out of the housing.

FIGS. 5–7 illustrate modifications to an instrument housing or operating head of a catheter which employs a plurality of optical beams to detect physical and/or chemical characteristics of the fluid exterior of the housing and fluid pressure. In FIG. 5, the end wall portion 72 of the tubular housing 71 of an instrument or head 70 of a catheter, is provided with a laterally extending or passageway 73 across which light is directed in two directions from either a single source or two sources thereof as described, one of which passes between opposite wall portions of the channel, while the other isfocused by means of a lens formation of the type illustrated in FIG. 4, beyond the end of the housing and reflected back to the bottom wall of the channel for the purpose illustrated in FIG. 4 and described above.

In FIG. 6, a cylindrical housing 75 defining the operating head of a catheter or enclosure of an instrument, contains a channel 77 extending around a portion of the end wall thereof to the side wall thereof. A light beam is illustrated as being projected laterally across such channel, preferably between the ends of respective transmitting and receiving light pipes or mirror-like surfaces as described which direct such light from the transmitting end of one light pipe to the receiving end of the other as described. Notation 78 referes to a lens formation centrally formed in th end wall 77 of the housing 75 for focusing light directed against its inside surface, as illustrated in FIG. 5.

FIG. 7 is an end view of FIG. 5 showing a similar lens formation 78 formed in the bottom wall of the channel 73 for focusing the light beyond the end of the housing, as illustrated in FIG. 5.

In FIG. 8, an instrument or operating head 80 of a catheter is formed with a cylindrical wall 81 having an end wall 82 containing a cavity 83 with a shelf molded in such end wall for supporting a diaphragm or thin disc 19 as described, to detect variations in fluid pressure by detecting variations in light reflected off the inside surface thereof. A cable 87 containing at least three light pipes extends axially along the central portion of the housing and terminates at a fitting 86 containing lens formations 89, 90 and 91 to its central lens formation 90 directs light from an external source through a convex lens 85 attached to and molded integral with an extension 84 of the inside surface of the side wall 81 of the housing and directs a portion of the light emitted from the central light pipe lens 90 against the inside surface of diaphragm 19 and a second portion thereof throughthe transparent end wall 83 of the housing. Reflections of said second portion of light are transmitted from the fluid medium outside of the housing back through the end wall 83 and through the lens 85 which is shaped to redirect such light through the end lens 91 of the third light pipe. Light received by the lens formations 89 and 91 are passed along respective light pipes of the cable 87 to respective deflection analyzing means located at the other end thereof. Notation 86 refers to a spacer or solid plug inserted into the housing 81 for retaining the cable 87 and the end fitting 88 thereof predeterminately within the housing for performing the functions described.

In FIG. 9, an instrument or operating head 92 of a catheter is formed of a circumscribing side wall 93 by injection molding a light transmitting plastic with an end wall 4 having a lens formation 95 bonded therein and a cavity 96 molded adjacent thereto. A first pair of light pipes 97A and 97B are supported by an insert or spacer 97 and terminate near the inside surface of the lens formation 95 for respectively transmitting light from an external source through such lens formation and receiving the reflected light therefrom after it has passed through a portion of the fluid medium adjacent the end wall 94 and transmitting such reflected light to a photoelectric detector for spectrographic analyzing means. A pair of light pipes 98 and 99 respectively terminate at a fitting 100 which contains a molded lens cap 101 having lens formations 101A and 101B formed of a single molding and operable for respectively focusing and receiving light directed to the head along pipe 98 directing such focused light against the rear surface of a diaphragm-like thin portion 94M of the molded front wall 94 of the head, which thin wall portion is operable to deflect with pressure aplied thereto by body fluid exterior of the head, as described, and to variably reflect such light to the lens formation 101B which directs same to the end of the light pipe 99 for transmission to the other end therefor to a sensor the output of which is computer processed and analyzed for detecting the pressure or pressure variations in the body fluid.

It is noted that certain of the features of the emdobiments of FIGS. 1 to 9 may be eliminated therefrom or combined with one or more of the other embodiments thereof as well as embodiments of one or more of the copending patent applications listed under Related Applications. For example, the embodiment of FIGS. 1 and 2 may include, in addition to means for electrooptically analyzing light passed through body fluid in the cavity 16 to determine such variables as identification of specific microorganisms such as specific cells, phages and virus existing in such fluid, the identification,by spectographic analysis with a computer, of certain chemical and biological elements and compounds in body fluid, such a blood and lymph fluid, digestive fluid and the like existing the the body duct in which the instrument or catheter is disposed. Additionally, it is noted that focused laser light of the type illustrated, may be employed at sufficient intensity to heat body fluid, specific elements therein such as specific cells, groups of cells, bacteria and virus, tissue cells, clot formations or other matter existing adjacent the end of side wall of the catheter for the purpose of killing, rendering ineffective or vaporizing same. Light directed along the same or a different path as that employed to vaporize or destroy select organisms or virus may be employed to detect same followed by a pulse or pulses of more intense radiation operable to effect such function of killing or vaporizing of individual organism. Detection of such individual cells, organisms or virus may be effected by computerized analysis of theimage signals derived by photoelectrically detecting the light reflected from and/or passed through such organisms and computer controlled analysis of the resulting image signals and their comparison with signals of known organisms derived from a memory with or without direct optical correlation between the light which is modulated with the image information derived from its reflection from such organisms. Employed per se or in combination with such computer controlled analysis of image signals and optical correlation to identify such organisms as exist in the body fluid scanned as described, may be automatic computer controlled spectographic analysis of the chemical and biological contents of the fluid by means of automatic spectography. Any of such techniques may be employed per se or in combination with one or more of the other two to generate a control signals upon detecting the presence of a particular organism in the fluid scanned, which control signal may be employed to pulse an auxilliary laser or to cause the scanning laser to increase the intensity of its beam or generate an auxilliary beam and direct same along substantially the same path as the detection beam so as to intersect and destroy or otherwise affect the organism just detected.

It is also noted that the light beam sensing means described may be employed with an instrument or catheter which is adapted to ingest a small quantity of body fluid by means of a valve controlled to open and admit such fluid to a chamber which is closed when the valve is closed thereafter, utilizing suction or capillary action to admit such sample of body fluid, after which the described light beam(s) is generated and passed through and/or reflected from such sample for the purpose described. If the cavities 16, 37, 56, 73, 74, etc. are replaced by capillary cavities, body fluid may be sampled and analyzed with light passed through such cavities as described.

In FIG. 10 is shown constructional details of a medical instrument in the form of a capsule to be ingested by swallowing and operable for sensing one or more physiological variables, as described and shortwave transmitting signals, either continuously or periodically, defining the variables sensed, to a shortwave receiver outside of the body. The device 102 includes electrical and optical means supported within a housing 103, which may be entirely or partly made of molded light transmitting material in two or more sections. The housing may vary from about ¼" to about 1" in diameter and ½" to 1½" long for use in the digestive tract or may be smaller for use in an artery. Centrally supported across and betwen opposite wall portions of housing 103 is an electrical assembly 110 including a circuit board or chip 111 defining a flat, multilayer rectangular substrate containing a thin disc shaped battery 112 secured thereto and connected for electrically energizing and powering circuit elements supported by such substate including one or more layers of microelectronic signal processing circuits which are connected to one or more pairs of photosensor-light source sensing arrangements supported along one or more borders or edges of such substrate. In FIG. 10 two sensing arrangements are shown, each at an opposite end of the flat rectangular substrate 111 and preferably defined by small flat chips or layers of respective light emitting and light sensing semiconducting material deposited on or preformed and automatically assembled along such edge portions of the substrate and electrically connected to corresponding circuit elements of the circuitry thereof. A light source 115 is secured to or formed in situ against an edge of the circuit board or chip 111 and is adapted to transmit its light through a lens formation 120 molded in a lens sheet 118 which is secured or molded against the edge of 111. The light is reflected from the rear surface of a thin wall portion 19 of the end wall of the capsule back through a second lens formation 119 molded in the sheet 118 to a photoelectric detector 117 which is similarly formed against or secured to the edge or border of substrate 111 and is connected to signal processing and analyzing circuitry of the substrate. A similar light source 114 and photoelectric detector or light sensor 115, supported along the other edge of the flat sunstrate 111 respectively transmit light through a lens formation 107 molded in the other end wall 106, are rereceive reflections of such light from the exterior fluid through a second lens formation 108 molded therein. The electrical signal output by sensor 115 is computer processed and analyzed by computing electrical circuits on the substrate 111 which generates electrical code signals indicative of the characteristics of the fluid and tissue so scanned and such code signals are shortwave transmitted to a shortwave receiver located exterior of the body, such as immediately adjacent the skin. A plurality of additional photoelectric detectors or sensor pairs, as shown in FIG. 11, may be provided along portions of the substrate 19 such as other edge portions thereof, for sensing light from one or more light sources located within the housing. Notation 113 refers to a shortwave antenna formed of a wire or a thin, flat metal strip-like conductor deposited against or etched from metal film bonded to either or both the major surfaces of circuit board 111. It is noted that while the housing 103 is preferably made of two half-sections, each injection molded of a light transmitting plastic resin, such as a polycarbonate, methyl-methacrylate or other suitable resin, just the end walls 104 and 106 thereof may be molded of such transparent plastic and may be shaped to easily assemble to the tubular central wall portion which may be made of two or more moldings of similar but not necessarily light transmitting resin. The interior surface of the central and end wall portions of the housing 103 may contain one or more formations, such as a ridge or ridges 109 shaped and located to align and retain the circuit board 111 and/or one or more lens sheets, such as 118, aligned with the circuit board and the end wall formations against or through which light is to be projected.

Light from source 116 is focused onto the rear surface of a thin sheet portion 19 of the front wall 104 of the housing 103. Such sheet 19 may comprise a separate thin sheet or membrane, as described, the border portion of which sheet is sealed or welded to a shelf behind an opening 105 in the front wall 104 in a manner to permit the thin sheet to deflect with pressure and such deflection to be photoelectrically detected by detecting variations in the light from light source 116 reflected and received by photosensor 117 which outputs corresponding electrical signals, which vary in accordance with variations in received light. Such variable electrical signals are processed and analyzed by microelectronic circuits located on or within the board or chip substrate 111. Substrate 111 also contains signal processing and analyzing electrical circuitry [not shown] which analyzes signals received from one or more of the sensors it mounts and generates coded electrical signals indicative of the variable sensed.

The circuit board 111 also contains formed on or assembled along the opposite edge or border portion thereof a second solid state light source 114 and photosensor 115 operable to receive light from said light source reflected from body fluid and tissue exterior of the housing. An end wall 106 of housing 103, molded of transparent plastic material, has a plurality of lens formations 107 and 108 molded therein for respectively directing light from light source 114, such as by focusing same at a point or area exterrior of the housing. Reflected light modulated with information on the body fluid or tissue it passes through and/ or is reflected off, is received by sensor 115 and detected by and modulates the sensing element of the sensor and causes a variable electrical signal to be generated on the output of the sensor.

It is noted that the capsule 102 may also contain and employ other types of sensors to sense different variables, such as bioelectrodes and the like exposed to fluid exterior thereof or injested therein through capillaries or controlled valves.

In FIG. 11, a substrate 122, such as the described printed circuit board or chip, has an edge portion 122E thereof abutting atransparent lens strip or sheet 125 containing individual focusing lens formations 126 formed in either or both surfaces thereof and operable to direct light from respective light sources 124 to a plurality of locations or points exterior of the housing and to receive reflections of such respective light beams and direct same to respective photoelectric sensors 127 formed along the edge of sheet 122E. Each of said light sources and photoelectric detectors may have the same characteristics or respective different operational characteristics for detecting different optical variables present in a body fluid being scanned. The lens sheet 125 may also contain different filter elements, defined by thin sheet-like formations of a filter material or materials deposited on either surface thereof to serve as filter media for transmitted and/or reflected light.

In FIG. 12, a circular disc 131 forms an assembly 130 of photoelectric sensors 133, denoted 133A, 133B, etc., which are circularly arrayed and assembled on or deposited around a surface of disc 131 about a central light source 132. The disc assembly 130 may be disposed at either or both ends of the capsule of FIG. 10 adjacent the circular end wall thereof containing corresponding lens formations aligned with light source 132 and photoelectric sensors 133 or may be disposed at the ends of the operating heads of the catheters of FIGS. 1 to 9. The photosensors 133A-133N, may each be operable to detect a different physiological phenomenon, such as a different microbiological element, enzyme or other chemical when such sensors operate per se or in combination with respective specially shaped lens formations aligned therewith on a lens sheet or end wall of the container 103, with or without corresponding filters applied to such lens sheet, in or on the sensors.

The structures and sensor arrays illustrated in FIGS. 11 and 12 may be employed in modified forms of the capsule of FIG. 10 or in modified forms of the catheters of FIGS. t to 9. For example, one or two of the arrays of FIG. 11 or the disc shaped assembly of FIG. 12 may be mounted at one end or both ends of the capsules of FIG. 10 while one of such sensor assemblies may be provided at the end of any of the catheters of FIGS. 1 to 9 for sensing a plurality of body fluid or tissue variables as described, by projecting and receiving light energy reflected from different portions of such fluid and transmitting the resulting electrical signals or light energy through the described conducting means, light pipe or electrical conductor, back along the catheter to a suitable receiving and detecting means at or beyond the other end of the catheter for analysis and control purposes as described.

In FIGS. 13 and 14 is shown details of a modified operating head of a medical instrument 140, such as a catheter adapted to be worked througha body duct and disposed at a select location therein or a rigid tube adapted to be inserted, for example, in a body cavity such as the mouth or anal cavity to dispose the end portion 142 thereof in contact with body tissue and fluid for the purpose of simultaneously detecting body temperature and fluid pressure or heartbeat.

Secured to and supported within the cylindrical wall 141 of the tube or capsule 140 is a mount 149 which centrally retains an electrical cable 150 within the interior volume of the container. Such electrical cable contains at least two insulated wire pairs in respective subcables 146 and 148. Wire pair 146 extends to a first transducer 145, such as a thermistor operable to sense temperature, the sensing end 145A of which extends to and slightly beyond the exterior surface 142S of the end wall 142 of the container so that it may engage body fluid and tissue of the cavity into which the instrument is inserted. The sensor 145 is preferably sealed within a subcavity 143 in the end wall 142 while a second sensor 147 is sealed within a second cavity 144 adjacent the cavity 143. The sensor 147 may comprise a microphone or any suitable pressure transducer operable to detect variations in fluid pressure and/or variations in blood pressure pulses, such as heart pulses, or heart sounds picked up through body tissue against which the end 142 of the instrument is disposed whenin a body cavity. It is noted that the assembly 140 may comprise part of an elongated probe assembly extending froma handheld housing containing signal processing and analyzing electrical circuitry together with a visual display or displays for temperature and pressure or may be connected to such a housing by means of a flexible cable, such as an extension of the cable 149 containing the subcable wire pairs 146 and 148.

In FIGS. 15 and 16 is shown a modified form of the temperature and pressure or pulse sensing device of FIGS. 13 and 14. The assembly 150 includes an elongated cylindrical tubular member or housing 151H having a rigid cylindrical wall 151 terminating at an arcuate or semi-spherical end wall portion 152 containing respective spaced-apart cavities 153 and 154 molded therein. Centrally disposed within the end portion of the tube 151 is an electronic assembly 155 formed of a rectangular circuit board or chip 156 containing a plurality of circuit elements including respective pairs of strip-like conductors 158 and 160 which respectively extend to a temperature sensor 157, such as a thermister deposited on or assembled along the front edge of the board 156 and a pressure transducer 159 similarly deposited on or assembled along the front end of board 156 adjacent to temperature sensor 157. The elements 157 and 159 are respectively disposed within respective cavities 153 and 154 molded in the front wall 152 of the housing. While such elements are shown recessed within the cavities 153 and 154, either or both may project through the cavities to the surface of the end wall or therebeyond for effecting suitable temperature and pulse or pressure measurements.

It is noted that the supports 149 and 156 of the embodiments of FIGS. 13 and 16 may also be employed to support a plurality of light pipes, such as the end portions of optical fibers or fiber optic bundles at the operating ends of the catheters to align same for the purposes described above. In other words, such mounts may be employed in the embodiments of FIGS. 1 to 9 to support the described light pipes in a manner to couple same to the optical components described.

In FIG. 17 is shown apparatus connected to the other ends of the catheters of FIGS. 1 to 9 and 13 to 16 wherein suitable modifications may be made, either to the operating ends of the catheters to provide the additional light communication channels or light pipes, such as fiber -optic bundles, necessary to effect two way communication as provided in FIG. 17 or the components of FIG. 17 may be reduced in number in order to accomodate just the number of light pipes shown in the drawings. In other words, each of the embodiments shown in FIGS. 1 to 9 and 13 to 16 may be provided with additional optical components including light pipes to permit them to be operated with the apparatus of FIG. 17 as described hereafter.

The apparatus 170 of FIG. 17 includes a hand holdable assembly 171 including an elongated housing 172 with a pistol-grip 172G for holding same and a trigger 179 for controllably closing a switch 189 for operating a laser 181 and electrically energizing a sensor or sensors located within a housing 183. The laser, which is supported on a mount 180 which also supports the housing 183 within the main housing 172, may be operable, as described elsewhere herein, to generate inspection radiation for viewing matter inside the body through an eyepiece 191 and for detecting the contents of such matter by means of the photoelectric detection means in housing 183 and/or spectographic detection means therein or located distal from the assembly 171. The laser 181 has its output connected to a first fiber-optical bundle 182 which extends through the center of the central portion 173 of the housing 172 to the far end 174 thereof and is supported by a plurality of bulkheads or recepticles 185 and 186 formed of or secured across the central and front end portions 173 and 174 of the housing 172. A manually operable coupling device 187 is operable to removably receive and retain a coupling 188 at the end of a flexible catheter tube assembly 10C for mechanically connecting the catheter tube to the end of the pistol-like assembly 171 and optically connecting three light pipes which extend the length of the catheter to the light pipes of the operating head thereof as illustrated in the drawings. If one or more additional lasers and/or photoelectric detectors are provided in the housing 172 for generating different types of laser light for visual and automatic inspection and/or for use in operating on tissue or other matter adjacent the end of the catheter and for receiving and analyzing such light after it has been modulated with tissue and fluid information as described, then both the catheter to be 10C and the assembly 172 will be modified to contain such additional light pipes and optical/ electro-optical components. Trigger operated switch 189 may thus be a normally open single pole switch which is operable when closed to connect the laser 181 and the photoelectric detector with a suitable source or sources of energizing electrical energy. If the laser 181 is operable at two or more levels of intensity or two or more lasers are provided to generate and transmit different types of laser light over the same or respective light pipes to the operating head of the catheter for performing different inspection and analysis or operating functions with respect to body fluid and/or tissue adjacent the operating head, then switch 189 may comprise a multiple pole and/or multiple throw switch operable by different degrees of pivotal movement of trigger 190 to energize the different lasers.

The rear wall 176 of the housing 172 contains a coupling 177 for connecting the light pipe output of a laser, such as a carbondioxide laser or an argon dye laser operable to generate intense light radiation capable of vaporizing tissue for operating purposes, to a fourth light pipe 178 which extends through housing 172 to the coupling 188 thereof or transmission of such intense light to the operating head through a respective fiber optic bundle or light pipe of the flexible catheter cable 10C. Also secured to and protruding rearwardly from the rear wall 176 is an eyepiece 191 connected to the end of a light pipe 192 which extends through the housing 172 to the coupling 187 and is coupled to receive light reflected from tissue and/or body fluid inside the body duct in which the operating head of the catheter is disposed. Sufficient optical fibers are contained within bundle 192 to provide a viewable image of the interior of the body duct on the viewing screen of the eyepiece 191.

An electrical cable 1945 is removably coupled to a connector 193 at the end of the pistol grip 172H for two-way communication and power supply between an externally located computer 195, a source of power for the electrical components and the laser 181 within the housing 172. The cable 194 preferably extends to a console containing a power supply 201 for the laser 181 and/or an external laser (not shown) optically coupled through the input 177 to a fiber-optic bundle in the catheter tube assembly 10C, a computer 195 for processing and analyzing the electrical signals output by the photoelectric detection sensor or sensors in housing 183, a keyboard 196 for operating the computer, a video display 199 and display buffer or driver 197,a magnetic recorder 199 for data generated by the computer, and a hard copy printer 200 for printing selected data generated by the computer. Laser power supply 201 is connected by a suitable switch 202, controlled by signals generated by a switch of the keyboard and/or a footswitch operated by the person operating the catheter, to selectively energize the laser 181 as well as a high power laser, is used for operating purposes, which is coupled to the input 177. The assembly 171 may also comprise an elongated housing without the pistol grip 172H which is hand held and may be supported or hung on a suitable stand located next to the person being examined and treated.

If a fluid, such as gas under pressure, or a liquid medication or coolant is employed to be pumped through a tube or passageway in the catheter tube 10C to the operating head of the catheter, it may be supplied from a reservoir through the handle or grip 172H or a line coupled to an input therefor located elsewhere on the housing and may be controllably pumped through suitable tubing in the housing 172 and the catheter tube 10C for use in the operation when needed by the physician.

Computer 195 is programmed to process and analyze the electrical signals output by the light sensor or sensors in housing and maye be operable to both image analyze and spectographically analyze by such analysis, the image and chemical and/or biological contents of body fluid sensed with light, as described, adjacent one or more locations of the operating head of the catheter. In a modified form of the apparatus shown in FIG. 17, one or more light pipes or fiber optic bundles may extend from respective light pipes extending through the catheter tube 10C from the head of the catheter, through the housing 172 and handle 172H to a spectrometer connected to or forming part of the computer 195 for effecting a comprehensive analysis of the information contained in the light reflected from and/or passed through the body fluid and/or tissue adjacent the head of the catheter to which the components of the apparatus 170 are connected or coupled.

If the photoelectric detectors shown in FIGS. 9, 11, 12, etc. are employed in the head of the catheter, then suitable flexible electrical conductors are provided extending through the catheter tube 10C and are electrically connected to conductors extending through the housing 172 to respective wiring in cable 194 to permit the signals so generated to be properly conducted to the computer 195 for processing and analysis thereby.

While the light pipes illustrated in the drawings have been described as fiber-optic bundles or bundles of optical glass fibers which are flexible and, as such, may be used in catheters to conduct light along the lengthof the catheter, as described, for those applications where it is desired to conduct high intensity light energy for burning or vaporizing tissue or other matter such as clotting material, light pipes formed of thin,flexible stainless steel tubing having highly reflective inside surfacing may be employed for one or more of thelight pipes shown in the drawings and may extend along the entire length of the catheter and/or through the operation head thereof. Such a light pipe which is sealed at its ends with suitable glass lenses or light conductors and filled with a gas, such as argon gas, may be employed to conducting high intensity laser light from a laser located exterior of the body, as described, to the operating head where it is directed therefrom directly into the body duct or through one or more optical components or lenses formed of the wall of the operating head or disposed across one ormore openings therein and sealingly secured thereto for focusing or otherwise directing such intense light.

Modifications to structures, systems and methods for operating and utilizing the medical instrument assemblies described and illustrated in the drawings are noted as follows:

1. The instruments and catheter assemblies illustrated in FIGS. 1 to 12 and described above including the described modifications thereto, may be used in a static mode for identifying single organism infections in vivo while disposed within a body duct of a living being by employing either or a combination of 'multiparameter light scattering, such as developed at the Los Alamos National Laboratory and 'flow cytometry', a method which has been used to identify and count large groups of molecules, by generating and directing high-intensity laser light through the light pipes of the embodiments of FIGS. 1 to 9 and through the transparent wall portions of the housings thereof to pass through and/or reflect off viral and bacterial organisms existing, for example, in the body fluid int eh cavities 16,37,56, 73,77,etc. or beyond the end and/or the side wall of the housings described. Either or both such techniques may be employed to rapidly identify such common viruses as influenze, herpes and encephalitis by photoelectrically sensing the externally focused and/or direct light beams directed as described and illustrated in the drawings against or through body fluid adjacent to and/or within a recess or cavity in the housing, and generating electrical analog signals which are digitized and computer analyzed by comparing the processed signals with so called 'fingerprint' or 'signature' signals derived from a memory and representative of the specific organisms to be identified. Such signal processing and analysis may take place in suitable microelectronic computing circuitry located in the catheter or capsule or by electronic computing means located externally of the living being being tested and coupled to the end(s) of the fiber optic cable(s) or light pipe bundle(s) described which extend from the described light receiving means 27,49,65,91,100,etc.

2. The capsule 102 of FIG. 10 may also contain the "multiparameter light scattering" and/or "flow cytometry" instrumentation described above for deriving and transmitting data indicative of such organisms, when detected thereby, to short wave receiving means located outside the body in which the capsule is disposed. The capsule 102 may effect such detection while freely travelling through a body duct, while adhesively attached to a select portion of the wall of the body duct or while otherwise implanted in tissue of the body by means of an incision made therein with a surgical tool.

3. For diagnostic purposes, including the detection of certain cancer cells whichmay be present in body fluid such as blood, lymph fluid and the like which are in contact with the housings of the embodiments of FIGS. 1 to 10, various types of lasers may be employed. Visible light from a kryton laser may be employed, for example, directed to the receiving end of one of the light pipes 22,46,63,64,97A,etc. froma laser located outside the body to be guided thereafter as described, in a manner to pass through or be reflected off body fluid and its microorganisms as described and to be directed to and along the described light pipes extending to the end of the catheter which islocated outside the body whee it is applied to one or more photoelectric detectors for the purposes described. Visible light from a Carbon dioxide laer or an argon dye laser may be pulsed and directed along one or more of the described light pipes from outside the body for use in deactivating or destroying microorganisms such as bacteria and/or virus or cancer cells in the path of such light as such organisms are detected as described.

4. If the structures illustrated in FIGS. 1 to 9 comprise parts of medical instruments, such as endoscopes or thelike, suitable light splitter means may be optically coupled thereto and operable to direct at least a portion of the received light to a spectroscope and/or spectrographic signal electronic computer analyzing circuitry located within the instrument and/or externally thereof for automatically detecting specific chemicals in the fluid scanned thereby. Such device may be used to detect and treat certain types of cancers as set forth in U.S. Pat. No. 4,566,057 and the reference thereof.

5. The catheter head structures illustrated in FIGS. 1 to 9 as well as the capsule of FIG. 10 may be formed, with the exception of the light pipes extending therethrough, by injection molding same of light transmitting glass, ceramic or plastic resin using single shot molding for forming two or more sections thereo which are bonded or welded together after aligning and holding respective portions of the light pipes therein. The lens, window and deflectable wall portions described may form respective portions of either or both the molded sections of the head housings together with other optical elements such as light splitting formations, light guides, diffusing means and the like.

6. Certain optical components, such as lenses, mirrors, prisms, light splitters, diffraction gratings, light guides, etc. may be separately formed and thereafter assembled in recepticle portions of one or both to the moldings forming the operating head of the catheter to properly guide and process ormodulate the light passing through the head. Such recepticle portions of the molding or moldings are so shaped to both retain and precisely align the optical components they accomodate. Retention may be effected by means of adhesive or solvent bonding or by frictional or locking means effected when the molded components are adhesive, or solvent bonded or welded together with the components are disposed in cavities formed therein by molding. Such separate optical components may be employed per so or in combination with optical components which are formed by molding transparent plastic forming all or part of the walls of the operating head.

7. So called multiple shot molding involving two or more different resins, two or more glasses or ceramic materials or a combination of glass, plastic and/or ceramic materials may be employed to form catheter operating heads of the types described. For example, opaque or non-optical material may be first molded of plastic resin, glass or ceramic material to form the major portion of the catheter end or head after which, optical resin, glass or ceramic material may be molded in situ against the first head forming material to form the optical components thereof such as mirrors, prisms, lenses, diffusers, light guides and the like.

8. The instrument structures illustrated in FIGS. 1 to 10 may be operable to modified to provide a plurality of additional paths for respective light beams generated by light sources located within the housings shown or transmitted thereto through the illustrated light pipes and/or one or more additional light pipes which are similarly supported within the housing as shown and extend thereto from one or more light sources located, for example, within or beyond a housing, such as provided in FIG. 17. Such plurality of different light paths may be such as to direct a plurality of beams of the same or different light, from a single or a plurality of light sources, through the same window or lens or a plurality of windows or lenses formed in the end wall and or side wall of the housing by molding same from a light transmitting plastic, glass or or ceramic material. Thus the instrument may be used, for example, to scan and detect matter existing along different paths in front of and/or adjacent the side wallof the housing for simultaneously or sequentially detecting the same or differnt organisms, chemical or biological elements or compounds in the fluid in which the instrument is disposed. Such scanning may be effected simultaneously and/or in a sequential manner under the control of a microprocessor or microcomputer which controls, for example, the energization of each of a plurality of different light sources, the multiplexing of light and/or electrical energy derived from a plurality of transducers located in the operating head and/or remote therefrom, as described and as shown, for example, in FIG. 17, to a computer for processing and analysis thereof. The plurality of such light paths which extend to respective windows or portions of a single window throughwhich the pluralityof light beams directed along such light paths may pass, may also be defined by light guides, mirrors, lenses, light diffusers, light splitters and the like which are either predeterminately retained and prcisely located within the housing defining the operating head and/or are molded of the same light transmitting plastic or glass of the which housing is molded.

9. The structures shown in FIGS. 1 to 10 as well as those of FIGS. 11 and 12 may be utilized in instruments other than catheters and other than meical instruments. Disposable, low cost structures of the types shown may be fabricated with all of the optical elements and the bulkheads or supporting structures for the light pipes as well as any wires employed to conduct electrical energy and molded of material forming the wall or walls of the housings shown. Such injection molded supporting structures may also be provided to support and precisely locate the illustrated and described photoelectric cells and light sources such as shown in FIGS. 8 and 9.

10. The medical instruments illustrated in FIGS. 1 to 9 and 17 may contain suitable light sources coupled thereto for generating two or more types of light energy, one or more for use in detecting organisms in body fluid, such as blood, by multiparameter light scattering; another for detecting other organisms or particles by flow cytometry; a third for use in detecting chemical compounds, enzymes and the like by means of spectrometry wherein the light reflected from the body fluid is analyzed by a computer controlled spectrometer. In the latter technique, the intensity of the light is preferably such as to vaporize or heat a small quantity of body fluid or tissue it intersects to prepare same for the spectographic analysis. as an inspection laser beam is directed thereat as described.

11. A plurality of laser beams may be generated and directed along the same or different paths through and beyond the operating head, as described, by a laser or a plurality of lasers, each containing light energy of a different wavelength than the others for providing a plurality of sources of different information when the direct light thereof or reflections thereof off body fluid are detected and analyzedunder the control of a computer which also controls the operations of the lasers by selectively gating same on and off, timing their operation and controllably increasing and/or decreasing the intensities of the light energies so generated.

12. As shown in FIG. 5, a plurality of laser light beams may be directed along respective paths through the operating head and directed from different light pipes which terminate at different locations of the side wall of the catheter to simultaneously scan the environment adjacent the side wall at different locations thereof. If the terminal locations of each light path or light pipe are staggered along thelength of the operating head and disposed one behind the other and are sufficient in number, then the instrument may be sud to scan the entire siewall of a body duct as it is moved therethrough for inspecting the condition of such side wall by generating electrical signals, each of which is representative of a strip or band-like portion of the length of the body duct so scanned. Such an inspection method may involve controlled movement of the instrument housing or catheter, such as by means of a motor drive, through the interior of a body duct such as an artery or veing or through a select portion of the digestive tract, while reflective scanning takes place with a plurality of light pipe pairs for transmitting and receiving laser radiation reflected from select strip-like portioons of the body duct wall arranged so as to scan the entire surface of the duct wall and provide electrical signals, as described, which may be computer processed and employed to provide a strip-like map or image of the inside surface of the body duct along the length thereof so scanned. Such image may be generated on a video viewing screen and/or formed as a strip chart or map on hard copy by suitable hard copy generating means.

13. Scanning and generating strip-chart like images of select lengths of the wall of a body duct may be effected by means of penetrating and reflecting radiation,such as ultrasonic energy and light energy, generated and applied simultaneously from an operating head of a catheter or instrument housing against a select portion of the wall of the body duct in which such housing is disposed while such housing is stationary or in controlled movement therethrough as described. A plurality of paralelly extending stripcharts representative of respective images of the internal structure and inside surface of the body duct may be thus generated by compute processing and analyzing electrical signals generated by a pulse-echo type utltrasonic transducer or a plurality of same disposed in the operating head and operable to transmit ultrasonic energy in the direction of the wall of the body duct and receive and convert reflections of such ultrasonic energy from the matter and tissue defining the duct wall to modulated electrical signals., simultaneously as scanning radiation of the type described in generated and reflected from the inside surface of the body duct and the reflected light is transduced to corresponding electrical signals. The two strip charts may be synchronously produced and located adjacent each other such that a person viewing both will be able to examine the visual graphical data relating to the internal structure of the duct wall and its surface structure and equate both for improving diagnosis and analysis. Depending on how the two forms of scanning radiation and generated and directed, the entire inside surface and wall of a select portion of a body duct may be so inspected and analyzed.

14. Electro-optical scanning of the inside of body duct, such as the fluid and/or inside surface of the wall thereof, may be effected by means of a single light source or laser and a wide-angle lens of radial light guide disposed at the end or or in communication with the end of a light pipe of the type described which is coupled to receive light from a laser. Such light may be caused to fan radially and reflect off substantially the entire inside surface of the duct and/or all duct contained fluid radial of the end of the cahtheter head or side wall and to receive the reflection of such light rom the fluid and body duct wall to provide a more detailed analysis of the body duct wall and/or the contents of the fluid in the duct, by the means described. Using such a wide angle lens or radial light guide, a plurality of sources of inspection light of different wave lengths may be simultaneously or intermittently directed therethrough to provide and inspection method for automatically analyzing different chemicals and biological elements present in the body fluid or blood by spectral analysis of the reflected light and/or signal processing of the electrical signals generate by one or more photodetecting elements receiving such reflected light energy.

15. Scanning body fluid in a body duct and the wall of the body duct as described,may be effected while the catheter or instrument houding is in controlled movement through the uct by means of controllably rotating one ormore ultrasonic transducers and/or light beam transmitting and receiving means, preferably by means of a controlled electric motor mounted in the catheter or instrument housing or at or beyond the end thereof which is exterior of the body, the output shaft of which supports or is connected to a mount for such transducer or transducing means, wherein suitable commutation of the electrical and/or light energy is provided along such shaft or an extension thereof. In an apparatus in which an ultrasonic pulse-echo transducer (or transducers) is operably rotated, within the instrument housing or catheter head,to scan radially thereof through the body liquid in the duct and the wall of the duct, such transducer may either slidably engage the inside surface of the cylindrical housing wall or be disposed in a coupling liquid filling the housig of the portion thereof containign the rotating transducer. The rotating transducer is thus sound wave coupled to the body fluid and duct wall through the liquid in the housing,the wall of the housing, the outside surface of which is surrounded by body fluid and/or is in contact withthe inside surface of the body duct wall. Either or both an ultrasonic pulse-echo type transducer and one or more light pipe transmitting receiving pairs or miniature light sources and photodetectors may be employed simultaneously or sequentially to effect such liquid, body duct wall and body duct structure scanning in a helical scanning path while the instrument housing or catheter is controllably moved throug the duct preferably as driven by a controlled electric motor therethrough.

16. A medical instrument embodying features of the invention described above may be employed with a control system therefore, such as one employing a digital computer for both effecting the automatic processing and analysis of scanning signals generated, as described, fromscanning matter adjacent the head or housing of the instrument to detect, when a scanning laser light beam intersects a particular organism in body fluid, a polyp or small tumor, a lesion or small wound in the body duct wall, and generate a control signal. Such control signal or signals may be employed to trigger the operation of a laser of one of the types described, for generating a pulse or pulses of laser light directed at the organism, growth or wound (such as an ulcer) for the purpose of vaporizing, burning or otherwise destroying or beneficially affecting same. Such pulse or pulses of corrective or sirgical radiation may be directed along the same path, including the same light pipe, as that along which the beam of inspection or detection radiation is directed so as to properly intersect the same organism, growth or wound in the duct wall intersected by the beamof inspection radiation. The computer may also be programmed and adaptively controllable to further scan the wound or growth and further control the operation of the laser used to treat same to cause such laser to generate suffiient radiation for a sufficient period of time or pulses necessary to properly treat and/or destroy the growth or wound. Additionally, the same or an auxilliary computer may be used to control one or more motors and drives for controllably moving the instrument through the body duct and, if used, controllably operating and moving a mirror or other optical means for deflecting and controlling the direction and path along which the laser beam is directed as well as its focus and intensity and/or the wavelength theeof for optimizing the treatment or surgical procedure. Such computer may include image signal analyzing computing means for analyzing image or light signals generated when the reflected light is photoelectrically detected, wherein the results of such computing includes the generation of control signals for controlling the operation of the laser or lasrs as described above for performing laser surgery on selected portions of the body duct, plaque adhered thereto, blood clots therein and the contents of the body fluid or blood carried thereby. Optical computing techniques, such as optical correlation and umage comparison techniques, may also be employed under the control of the computer per se or in combination with the computerized image signal processing and analysis to provide such instrument automatic control during surgical and corrective surgical operations on select portions of the body duct wall and/or matter adhered thereto, clogging or consticting the body cavity or vessel.

Computer processing and analysis of the signals generated on the output of the described pulse-echo ultrasonic transducer or transducers employed to scan the body duct wall may also be employed to detect tumors, polyps, wounds or ulcers and the like which are corterized or corrected upon detection by automatically controlling the operation of one or more lasers or other forms of radiation generation means for generating and applying such radiation to the portion of the body duct wall requiring such treatment.

Such computer processing and analysis of ultrasonic pulse signals derived fromsound pulses reflected off constricting matter, such as blood clots and plaque deposited on the wall of the body duct may also be employed to generate control signals for controlling the generation and direction of intense radiation, such as by means of a laser, to cause same to reduce or eliminate such constricting material by vaporizing or burning same and/or by causing select amounts thereof to become detached from their constricting location and to flow therefrom and be expelled from the body by natural means or by means of a trap including a filter secured to the instrument across a passageway therethrough which the body fluid flows through and/or is pumped. If the quantity of the constricting matter is removed in small amounts it may be so removed by natural and/or filtering means associated with the instrument disposed in the body duct as described.

I claim:

1. A medical instrument comprising:
   (a) a support,
   (b) an operating head having side and end walls supported by said support, wherein said side and end walls form a cavity region inside of said operating head,
   (c) a recess in one of said walls, said recess being defined by light transmissive walls and; a diaphragm supported by said light transmissive walls which moves with respect to said head cavity when subjected to pressure differences between the cavity pressure and the surrounding body pressure.
   (d) a first light transmission means in said cavity for directing light to said diaphragm,
   (e) a first measurement means for receiving light reflected from said diaphragm and for measuring pressure therefrom,
   (f) a second light transmission means for directing light through said recess walls, whereby light passes through a first wall from said cavity, into said recess, then into a second wall of said recess and back into said cavity, and
   (g) a second measurement means for receiving said second light transmission light which passes back into said cavity and for measuring parameters of matter in said recess from the received light.

2. The apparatus in accordance with claim 1 wherein said first and second light transmission means includes a fiber optic conductor which carries light into said cavity.

3. The apparatus in accordance with claim 2 wherein said first and second light transmission means further includes a beam splitter means located in said cavity to split the light from said fiber optic.

4. The apparatus of claim 2 wherein said recess is located on a side wall of said operating head.

5. The apparatus in accordance with claim 1 wherein said diaphragm is located at the deepest portion of said recess.

6. The apparatus of claim 1 wherein said recess is located adjacent the end wall of said operating head.

7. The apparatus of claim 1 wherein said recess is located on a side wall of said operating head.

8. The apparatus of claim 1 further comprising a third measurement means for directing light through a wall of said operating head and for measuring light reflected back to said cavity from matter located outside of said cavity.

* * * * *